United States Patent [19]

Brown

[11] Patent Number: 6,066,670
[45] Date of Patent: *May 23, 2000

[54] THERAPEUTIC COMPOSITIONS AND METHODS OF USE

[76] Inventor: Raymond K. Brown, 140 W. 69 St., #105A, New York, N.Y. 10023

[ * ] Notice: This patent issued on a continued prosecution application filed under 37 CFR 1.53(d), and is subject to the twenty year patent term provisions of 35 U.S.C. 154(a)(2).

[21] Appl. No.: 08/564,088

[22] PCT Filed: Jun. 8, 1994

[86] PCT No.: PCT/US94/06653

§ 371 Date: Dec. 8, 1995

§ 102(e) Date: Dec. 8, 1995

[87] PCT Pub. No.: WO94/28883

PCT Pub. Date: Dec. 22, 1994

[51] Int. Cl.⁷ .................................................. A01N 37/00
[52] U.S. Cl. ............................................. 514/557; 514/574
[58] Field of Search ...................................... 514/557, 574

[56] References Cited

U.S. PATENT DOCUMENTS 4,828,912  5/1989  Hossain et al. ......................... 428/289

OTHER PUBLICATIONS

Poli et al 91 CA 187263g 1979.

*Primary Examiner*—Russell Travers
*Attorney, Agent, or Firm*—Mitchell A. Stein; Stein Rosenfeld & Kaplan, LLP

[57] ABSTRACT

According to the present invention, there is provided an admixture of sorbic acid, malic acid, fumaric acid, crotonic acid, and optionally aconitic acid. Further contemplated by the present invention are methods for treating various pathological conditions such as viral infections, acidosis, tumors, and bacterial and fungal infections by administering various therapeutically effective amounts of an admixture described above.

8 Claims, No Drawings

THERAPEUTIC COMPOSITIONS AND METHODS OF USE

This application is a 370 of PCT/US94/06653 filed Aug. 6, 1994, which claim priority from U.S. patent application Ser. No. 08/073,934 filed Jun. 8, 1993, now abandoned.

FIELD OF THE INVENTION

The invention relates to admixture compositions of short chain organic fatty acids which have biological effects. For example, they are useful in the treatment of numerous pathologies that affect mammals. The invention also relates to methods of treatment of such pathologies, wherein appropriate therapeutically effective amounts of the compositions are administered.

BACKGROUND OF THE INVENTION

A wide variety of carboxylic acid containing compositions are biologically active, and several short chain organic acids which are naturally occurring acids have previously been implicated in the treatment of various pathological conditions. For example, Nordman, U.S. Pat. No. 3,291,689, discloses the treatment of hepatic ammonia intoxication with a mixture of L-arginine and malic acid. U.S. Pat. No. 3,718,664 discloses the use of thioctic acid derivatives in the treatment of acidosis.

Sloan, U.S. Pat. No. 4,381,307, discloses soft tertiary amine ester derivatives that have biological effects, while U.S. Pat. No. 4,760,078 discloses a 1,2, dithiol-3-thione derivative that has an immunomodulating effect.

Rubenstein, U.S. Pat. No. 4,971,760, discloses the sterilization of blood, blood constituents, and transplant tissues with a disinfectant that includes lactic acid and sodium chlorite. Naphtholic acid derivatives were discovered to be useful in enhancing oxygen availability to mammalian tissue by Suh et al., U.S. Pat. No. 5,015,663.

Hoffiler et al., U.S. Pat. No. 5,043,357, disclose a virucidal agent that is predominantly comprised of ethanol and/or alcohol but which includes a minor amount of a short chain organic acid. Further, U.S. Pat. No. 5,093,140 discloses an aqueous bactericide that contains organic acids. This solution is used in the scalding or washing stages of meat dressing. Kross et al., U.S. Pat. No. 5,100,652 disclose an oral disinfectant that contains organic acids. See also Comroe et al., The Lung, 1955 Yearbook of Medical Publications Inc., Chptr. 4; John West, *Respiratory Physiology*, The Williams & Wilkins Co., Chptr. 6; Hypoxia, *Metabolic Acidosis and Circulation*, ARTCF . . . Oxford; Arnold et al, "Excessive Intracellular Acidosis of Skeletal Muscle on Exercise in a Patient with a Post-Viral Exhaustion/Fatigue Syndrome" *The Lancet*: Jun. 23, 1984; Schweckendiek, W., "Heilung von Psoraiasis vulgaris", *Med. SschS*, 13:103–4, 1959; G. E. Abraham et al., "Rationale for the Use of Magnesium and Malic Acid", *Journal of Nutritional Medicine,* 3:49–49 (1992); Kuroda, Z. and Akano, M., "Antitumor and Anti-intoxication Activities of Fumaric Acid in Cultured Cells", *Gann,* 727:77–782 (1981); *Chemical Abstracts* 98945Y, 116, March 1992 "Antifungal Activity of Fumarates in Mice Infected with C. Albicans"; Bauer et al., "Clinishe Wochenschrift 1991 69(2), pp. 722–4; for further details of several pathological processes which are susceptible to treatment according to the present invention.

It has now been discovered that admixtures of specific short chain organic acids have broad therapeutic effects.

SUMMARY OF THE INVENTION

According to the present invention, there is provided a composition which comprises an admixture of sorbic acid, aconitic acid, malic acid, fumaric acid, crotonic acid, and optionally aconitic acid.

Further contemplated by the present invention are methods for treating various pathological conditions such as viral infections including, but not limited to, cytomegalovirus and hepatitis infections; acidosis; tumors; and bacterial and fungal infections, by administering various therapeutically effective amounts of the admixture described above.

DETAILED DESCRIPTION OF THE INVENTION

Organic acids are a large group of compounds, many of which can be derived from proteins, carbohydrates, and fats. Although many occur naturally, many can be synthetically produced without great difficulty.

Sorbic acid is a crystalline diolefinic acid having the formula $C_6H_8O_2$. Typically, it is used as mold and yeast inhibitor; a fungistatic agent for foods, especially cheeses; or to improve the characteristics of drying oils, the gloss of alkyd type coatings, or the milling properties of cold rubber.

Aconitic acid is a white crystalline acid having the formula $C_6H_6O_6$. Typically, it is used in manufacturing itaconic acid or as a plasticizer for buna rubber and plastics.

Malic acid is a crystalline dicarboxylic acid having the formula $C_4H_4O_5$ and is typically found in three isomeric crystalline forms.

Fumaric acid is a crystalline unsaturated dicarboxylic acid having the formula $C_4H_4O_4$. Fumaric acid is typically used as a substitute for tartaric acid in beverages and baking powders, as a replacement or partial replacement of citric acid in soft drinks, and as an antioxidant.

Crotonic acid is an unsaturated aliphatic acid having the formula $C_4H_6O_2$. It exists in the crystalline form, and is typically used in the manufacture of copolymers with vinylacetate that are used in lacquers and paper sizing, and in the manufacture of softening agents for synthetic rubber.

It has now been discovered that these acids, in combination, have significant therapeutic value. The admixtures of these acids are prepared by conventional means known to those skilled in the skilled art. The order of addition of the acids to the admixture does not affect the final composition.

Although a wide range of proportions of the individual components of the admixture is effective, in a typical composition, each of the four required individual acids will independently comprise from about 1 to about 50 parts by weight and, optionally, aconitic acid will comprise from 0 to about 50 parts by weight, based upon 100 parts by weight of the five acids combined. Preferably, sorbic acid comprises from about 5 to about 40 parts by weight, aconitic acid comprises from 0 to about 50 parts by weight, malic acid comprises from about 1 to about 30 parts by weight, fumaric acid comprises from about 1 to about 30 parts by weight, and crotonic acid comprises from about 1 to about 30 parts by weight, based upon 100 parts by weight of the five acids combined. Most preferably, sorbic acid comprises from about 20 to about 30 parts by weight, aconitic acid comprises from about 35 to about 45 parts by weight, malic acid comprises from about 10 to about 20 parts by weight, fumaric acid comprises from about 10 to about 20 parts by weight, and crotonic acid comprises from about 1 to about 20 parts by weight, based upon 100 parts by weight of the five acids combined. Special mention is made of an admixture wherein sorbic acid comprises about 24 parts by weight, aconitic acid comprises about 40 parts by weight, malic acid comprises about 16 parts by weight, fumaric acid comprises about 16 parts by weight, and crotonic acid comprises about 4 parts by weight, based upon 100 parts by weight of the five acids combined.

Suitable pharmaceutically active carriers may be combined with the admixture. Such carriers include those known to those skilled in the art and can be added at any point in the mixing process. If a pharmaceutically active carrier is used, the carrier will comprise from about 1 to about 99 parts by weight and the acid admixture will comprise from about 99 to about 1 part by weight, based upon 100 parts by weight of acid admixture and carrier combined.

The acid admixture with or without the carrier can be formulated into dosage unit forms including, but not limited to, capsules and tablets. Methods of preparation of dosage unit forms would be known to those skilled in the art. Agents which facilitate the manufacture and/or use of such dosage unit forms may be added such as plasticizers, lubricants, excipients, diluents and the like.

Methods of treatment of various pathologies contemplated by the present invention involve the administration of therapeutically effective amounts of the admixture to mammals in need of such treatment. Administration is by means known to those skilled in the art. Preferably, administration is systemic and most preferably, it is oral.

Pathologies which are effectively treated with the organic acid admixture described herein include but are not limited to acidosis; viral infections including, but not limited to, cytomaglovirus and hepatitis infections; tumors; and bacterial and fungal infections, including but not limited to *S. aureus, E. coli*, and *C. albicans*.

All of these pathologies are well known to those skilled in the art, and their diagnosis would be evident to one skilled in the art. For example, acidosis is reflected by abnormally acidic blood pH and/or urine pH. Normal blood pH ranges from about 7.3 to about 7.38, and normal urine pH ranges from about 6 to about 8. Viral, bacterial, and fungal infections can be confirmed by appropriate assay methods. Other diseases such as chronic fatigue syndrome are only diagnosed through clinical observations. Various opportunistic infections which are characteristic of AIDS including, but not limited to, cytomegalovirus, hepatitis, and the like are effectively treated as described herein.

The amount of the admixture necessary to treat acidosis is an anti-acidosis effective amount. Similarly, the amounts of the admixture necessary to treat a viral infection, and particularly hepatitis and cytomegalovirus infections are an anti-viral effective amount, and particularly anti-hepatitis and an anti-cytomegalovirus effective amounts. The amount required to treat tumors, and bacterial and fungal infections are anti-tumor, anti-bacterial, and anti-fungal effective amounts, respectively.

The actual amounts of the admixture to be administered will depend independently upon the age, weight, sex, sensitivity, medical condition, including but not limited to stage of a particular infection or disease, or the like, of an individual. However, the amount will be a safe non-toxic amount.

These amounts can be determined by experimentation well-known in the art such as by establishing a matrix of dosages and frequencies and assigning a group of experimental subjects to each point in the matrix. Typically, that amount will range from about 1000 to about 2000 milligrams per day for a 150 pound man and preferably about 1500 milligrams per day for a 150 pound man. Appropriate dosages for different body weights can be calculated from this.

A daily dosage identifies the average amount of the mixture administered to an individual. Although the daily dosage may actually be administered daily, it need not be administered daily. The daily dosage is merely an average dosage that an individual receives when the mixture is administered over a period of time. The daily dosage can be administered in divided portions so that the total amount administered is the daily dosage.

DESCRIPTION OF THE PREFERRED EMBODIMENTS

The following examples illustrate the invention without limitation. All amounts are given as parts by weight (pbw).

EXAMPLE 1

An admixture of 24 parts by weight of sorbic acid, 40 parts by weight of aconitic acid, 16 parts by weight of malic acid, 16 parts by weight of fumaric acid, and 4 parts by weight of crotonic acid was applied, in various dilutions, to cut filter paper, and the filter paper was overlayed on plates streaked with bacteria. Results are illustrated in Table 1.

TABLE 1

| Admixture Dilution | Bacterial Assays | | | | | |
|---|---|---|---|---|---|---|
| | Aspergillus | Staph. aureus | Pseudomonas aeruginosa | Escherichia coli | Candida albicans | pH |
| Full Strength | – | 1.6 cm | – | 1.1 cm | 1.6 cm | 2.2 |
| 1:10 | – | – | – | – | – | 4.6 |
| 1:100 | – | – | – | – | – | 5.2 |

The (–) negative means that no inhibition was observed.

EXAMPLE 2

A patient had a temperature of 101° F. and symptoms of acute urinary and prostate infection. The patient was treated with 1500 mg/day of an admixture of 24 pbw of sorbic acid, 40 pbw of aconitic acid, 16 pbw of malic acid, 16 parts by weight of fumaric acid, and 4 pbw of crotonic acid based upon 100 pbw of total admixture for ten days. Symptoms and temperature subsided by the 4th or 5th day. Antimicrobial and alkalizing activity and therapeutic effects of the admixture are illustrated in Table 2. Cultures which were positive for streptococci were negative by the third week.

TABLE 2

| | Urinary Infection | | |
|---|---|---|---|
| Laboratory Test | Initial Treatment Day 1 | Day 10 | Day 32 |
| URINALYSIS | | | |
| pH | 5.5 | 8 | 6 |
| Protein | 1+ | 0 | 0 |
| WBC | 20–30 | 2–4 | 2–4 |
| Bacteria | many | 0 | few |
| Urine Culture | Strept. + | ± | 0 |
| Blood PSA (normal 0–4) | 21.9 | 5.1 | 3.22 |
| WBC | 10.4 | | 6.1 |

EXAMPLE 3

Six HIV positive individuals with average urine pH at breakfast, lunch, and dinner of 6.0, as measured by pHydrion tape, were administered 1500 mg/day of an admixture of 24 pbw of sorbic acid, 40 pbw of aconitic acid, 16 pbw of malic acid, 16 pbw of fumaric acid, and 4 pbw of crotonic acid.

After one month, average urine pH was raised to 6.3. Previously, it was fixed at 6.0. Results are illustrated in Table 3 below.

TABLE 3

Acidosis

| Patient | Urine pH Breakfast | Urine pH Lunch | Urine pH Dinner |
|---|---|---|---|
| "A" | 6.0 | 6.2 | 6.2 |
|  | 6.0 | 6.2 | 6.0 |
|  | 6.4 | 6.2 | 6.2 |
| "B" | 6.2 | 6.4 | 6.2 |
|  | 6.0 | 6.0 | 6.4 |
|  | 6.2 | 6.4 | 6.2 |
| "C" | 6.0 | 6.0 | 6.2 |
|  | 6.0 | 6.2 | 6.0 |
|  | 6.0 | 6.0 | 6.2 |
| "D" | 6.0 | 6.0 | 6.2 |
|  | 6.0 | 6.2 | 6.2 |
|  | 6.0 | 6.0 | 6.2 |
| "E" | 6.0 | 6.4 | 6.4 |
|  | 6.2 | 6.2 | 6.2 |
|  | 6.0 | 6.0 | 6.2 |
| "F" | 6.0 | 6.4 | 6.4 |
|  | 6.2 | 6.2 | 6.2 |
|  | 6.0 | 6.2 | 6.2 |

EXAMPLE 4

A patient with urine culture positive for cytomegalovirus infection was treated with 1500 mg/day of an admixture of 24 pbw of sorbic acid, 40 pbw of aconitic acid, 16 pbw of malic acid, 16 pbw of fumaric acid, and 4 pbw of crotonic acid, based upon 100 pbw of total admixture for six weeks. After six weeks, a cytomegalovirus urine culture was negative.

EXAMPLE 5

A patient having cancer of the prostate with a PSA of 17 was treated with Zolodex™. PSA was lowered to 2.4. Seven months after Zolodex treatment was discontinued, PSA rose to 13.

The patient then received 1500 mg/day of an admixture of 24 pbw of sorbic acid, 40 pbw of aconitic acid, 16 pbw of malic acid, 16 pbw of fumaric acid, and 4 pbw of crotonic acid based upon 100 pbw of total admixture, and PSA was lowered to 1.65. Nightly urination decreased from 5–6 times/night to two times/night and the patient's general energy increased 80%.

EXAMPLE 6

A patient was diagnosed with a pancreatic mass. The patient also had nausea, pain, an inability to eat, weight loss, and weakness.

The patient, who weighed about less than eighty pounds, was given 50 mg/day of an admixture of 24 pbw of sorbic acid, 40 pbw of aconitic acid, 16 pbw of malic acid, 16 pbw of fumaric acid, and 4 pbw of crotonic acid based upon 100 pbw of total admixture for two months. The patient's nausea abated, her appetite improved, she slept more restfully, and she did not urinate as frequently at night. The epigastric mass was no longer palpable.

EXAMPLE 7

A patient underwent a resection of a recurrent bladder tumor, at which time, the pathological specimen revealed Grade II/III moderately differentiated papillary transitional cell carcinoma with invasion of the muscularis of the urinary bladder and of the prostate. The patient was placed on a protocol of 1500 mg/day of an admixture of 24 pbw of sorbic acid, 40 pbw of aconitic acid, 16 pbw of malic acid, 16 pbw of fumaric acid, and 4 pbw of crotonic acid based upon 100 pbw of total admixture. A repeat cystoscopy two months later showed only several small papillary lesions in the urinary bladder and a small lesion in the prostatic urethra. Rectal examination was unremarkable. CAT SCAN confirmed the improvement observed by cystoscopy.

EXAMPLE 8

A patient was diagnosed with long standing Hepatitis C. The patient was treated with 1500 mg/day of an admixture of 24 pbw of sorbic acid, 40 pbw of aconitic acid, 16 pbw of malic acid, 16 pbw of fumaric acid, and 4 pbw of crotonic acid based upon 100 pbw of total admixture. After one month, pain in the patient's side subsided. The patient was no longer nauseated and generally felt better. His SGOT laboratory value went down from 68 to 37.

EXAMPLE 9

An admixture of 24 pbw of sorbic acid, 40 pbw of aconitic acid, 16 pbw of malic acid, 16 pbw of fumaric acid, and 4 pbw of crotonic acid based upon 100 pbw of total admixture was tested for virucidal effectiveness against Cytomegalovirus. The viral inoculum was diluted 1:10 with the admixture. The test material/virus mixture was sampled at 3 and 6 minutes. The treated viral mixture was neutralized and titered. An initial viral titer was determined.

The challenge organism was Cytomegalovirus, (CMV) and the host cell line was MRC-5, ATCC CCL-171. Reagents and media were EMEM with Earle's salts supplemented with heat inactivated fetal bovine serum (FBS), glutamine, and penicillin streptomycin (MEM complete); sterile phosphate buffered saline; and newborn calf serum (NBCS).

The virus stock culture was titered and adjusted to contain approximately $10^7$ CCID$_{50}$/ml (50% cell-culture infectious doses per milliliter) and stored in liquid nitrogen until use. The virus stock was thawed and was diluted 10-fold in MEM through $10^{7.}$ One ml aliquots of appropriate dilutions were plated onto 5 confluent MRC-5 monolayers. The cells were incubated at 37±1° C., in 5% $CO_2$, for 2 hours to allow the virus to adsorb to the cells. After adsorption, the medium was withdrawn from the monolayers, the cells were washed once with PBS, and refed with MEM. The monolayers were incubated for 14 days at 37±1° C., in 5% $CO_2$, and subsequently were observed for virus-specific cytopathogenic effects (CPE).

The test solution was tested by combining the virus with the admixture at a 1:10 dilution. This suspension was agitated continuously at a constant temperature of 25° C. and samples were withdrawn at 3 and 6 minutes to determine a survivor curve and to calculate a D-value.

The sampled suspensions were neutralized with a 1:1 dilution in new-born calf serum and were diluted ten-fold in MEM. One ml aliquots of the neutralized mixture were plated onto MRC-5 monolayers (four wells per dilution) and were incubated at 37∓1° C. in a 5% $CO_2$ in air atmosphere for 2 hours. Following the incubation period, the fluids were removed. The monolayers were washed with PBS, refed MEM and were incubated at 37±1° C. in a 5% $CO_2$ in air atmosphere for thirteen days.

Control virus stock was titered at the time of the test as described, to confirm that the titer was in an acceptable range. The maintenance of the virus titer was evaluated using PBS instead of the test solution. Samples were taken less than 15 seconds after the initiation of the test (zero time control) and after 6 minutes (final time control). The average $CCID_{50}$/ml for each titer was determined by the Reed and Muench method. *American Journal of Hygiene,* 1938, 27:493. The D-value was calculated by the Stumbo method. Stumbo, C. R., *Thermobacteriology in food processing,* New York Academic Press (1973), pp. 235–247.

No CPE was observed at 3 minutes. A D-value calculated using this time resulted in a D-value of 45 seconds. This is an estimate since the first sampling was done at 3 minutes (no data were collected at less than 3 minutes).

When a survivor curve was determined in this test, the admixture provided data used to calculate a D-value of 45 seconds (estimated). A conclusion can be drawn that the admixture was antiviral against cytomegalovirus.

Results are illustrated in Tables 4, 5, and 6 below.

TABLE 4

Test and Control Titers Expressed as CPE
Day 13 Results

| DILUTION | VIRUS STOCK | PBS Zero | PBS 6 min | TEST SOLUTION 3 min | TEST SOLUTION 6 min |
|---|---|---|---|---|---|
| $10^{-1}$ | NA | ++++ | ++++ | ---- | ---- |
| $10^{-2}$ | ++++ | ++++ | ++++ | ---- | ---- |
| $10^{-3}$ | ++++ | ++++ | ++++ | ---- | ---- |
| $10^{-4}$ | ++++ | +-+- | +-+- | ---- | ---- |
| $10^{-5}$ | ++++ | ---- | ---- | ---- | ---- |
| $10^{-6}$ | ---- | ---- | ---- | ---- | ---- |
| $10^{-7}$ | ---- | N/A | N/A | N/A | N/A |
| $CCID_{50}$/ml | $3.2 \times 10^5$ | $1 \times 10^4$ | $1 \times 10^4$ | | |

+ = CPE observed
− = No CPE observed
CT = Cytotoxicity observed
O = No Cytotoxicity observed

TABLE 5

Control and Test Titers at Time Intervals
After Exposure to Scam Disinfectant

| SAMPLE | $CCID_{50}$/ml |
|---|---|
| Sample | $3.2 \times 10^5$ |
| PBS at Zero time | $1 \times 10^4$ |
| PBS at 6 minutes | $1 \times 10^4$ |
| 3 minutes | No CPE observed |
| 6 minutes | No CPE observed |

TABLE 6

Determination of the D-Value $$D = \frac{Tx - To}{\text{Log } Ao - \text{Log } Ax} = \frac{3 - 0}{\text{Log } 10^4 - 0} = \frac{3}{4} = 0.75 \text{ min} = 45 \text{ seconds}$$

Tx = end of time interval
To = beginning of time interval
AO = $CCID_{50}$/ml at To
AX = $CCID_{50}$/ml at Tx

EXAMPLE 10

A 36 year old male with well controlled HIV infection had progressively deteriorating kidney function from no demonstrable cause. He averaged 5× nocturia and ran a consistently 3 plus albuminuria with urinary specific gravity fixed at 1.005 (normal to 1.030).

After approximately 4 months of 1500 mg/day of admixture of 24 pbw of sorbic acid, 40 pbw of aconitic acid, 16 pbw of malic acid, 16 pbw of fumaric acid, and 4 pbw of crotonic acid based upon 100 pbw of total admixture, his kidney function normalized. His three plus albuminuria gradually became negative; he became able to sleep through nights, and the specific gravity of his urine by concentration test increased to 1.0020. His urinary pH, which had been fixed at 5–6 resumed a normal pattern of morning aciduria, increasing to neutral or alkaline during the day according to his diet and activity.

Accompanying this was a total regression of his long-existing bilateral massively swollen parotid glands; the non-specific diagnosis derived from multiple biopsies had been cystic parotitis. The presumptive retro-diagnosis for parotitis and the kidney insufficiency was severe cytomegalovirus (CMV) infection, suggested by high titers of CMV antibodies.

The above mentioned patents, test methods, and publications are hereby incorporated by reference in their entirety.

Many variations of the present invention will suggest themselves to those skilled in the art in light of the above detailed description. All such obvious variations are within the full intended scope of the appended claims.

What is claimed is:

1. A method for treating a viral infection in a mammal in need of such treatment comprising orally administering to said mammal, in a systemic, in vivo manner, an anti-viral effective amount of a composition comprising an admixture comprising:

(a) sorbic acid;
    (b) malic acid;
    (c) fumaric acid;
    (d) crotonic acid; and
    (e) aconitic acid.

2. A method for treating cytomegalovirus infection in a mammal in need of such treatment comprising orally administering to said mammal, in a systemic, in vivo manner, an antic-cytomegalovirus effective amount of a composition comprising an admixture comprising:

(a) sorbic acid;
    (b) malic acid;
    (c) fumaric acid;
    (d) crotonic acid; and
    (e) aconitic acid.

3. The method of claim 1, wherein each of components (a), (b), (c), and (d) independently comprise from about 1 to about 50 parts by weight, and component (e) comprises from 1 to about 50, based upon 100 parts of by weight of (a), (b), (c), (d), and (e) combined.

4. The method of claim 2, wherein each of components (a), (b), (c), and (d) independently comprise from about 1 to about 50 parts by weight, and component (e) comprises from 1 to about 50, based upon 100 parts of by weight of (a), (b), (c), (d), and (e) combined.

5. The method of claim 1, wherein component (a) comprises from about 5 to about 40 parts by weight, component (b) comprises from about 1 to about 30 party by weight, component (c) comprises from about 1 to about 30 parts by weight, and component (e) comprises from about 1 to about 50 parts by weight, based upon 100 parts by weight of components (a), (b), (c), (d) and (e) combined.

6. The method of claim 2, wherein component (a) comprises from about 5 to about 40 parts by weight, component (b) comprises from about 1 to about 30 party by weight, component (c) comprises from about 1 to about 30 parts by weight, and component (e) comprises from about 1 to about 50 parts by weight, based upon 100 parts by weight of components (a), (b), (c), (d) and (e) combined.

7. The method of claim 1, wherein component (a) comprises from about 20 to about 30 parts by weight, component (b) comprises from about 10 to about 20 parts by weight, component (c) comprises from about 10 to about 20 parts by weight, component (d) comprises from about 1 to about 20 parts by weight, and component (e) comprises from about 35 to about 45 parts by weight, based upon 100 parts by weight of components (a), (b), (c), (d) and (e) combined.

8. The method of claim 2, wherein component (a) comprises from about 20 to about 30 parts by weight, component (b) comprises from about 10 to about 20 parts by weight, component (c) comprises from about 10 to about 20 parts by weight, component (d) comprises from about 1 to about 20 parts by weight, and component (e) comprises from about 35 to about 45 parts by weight, based upon 100 parts by weight of components (a), (b), (c), (d) and (e) combined.

\* \* \* \* \*